Figure 1:
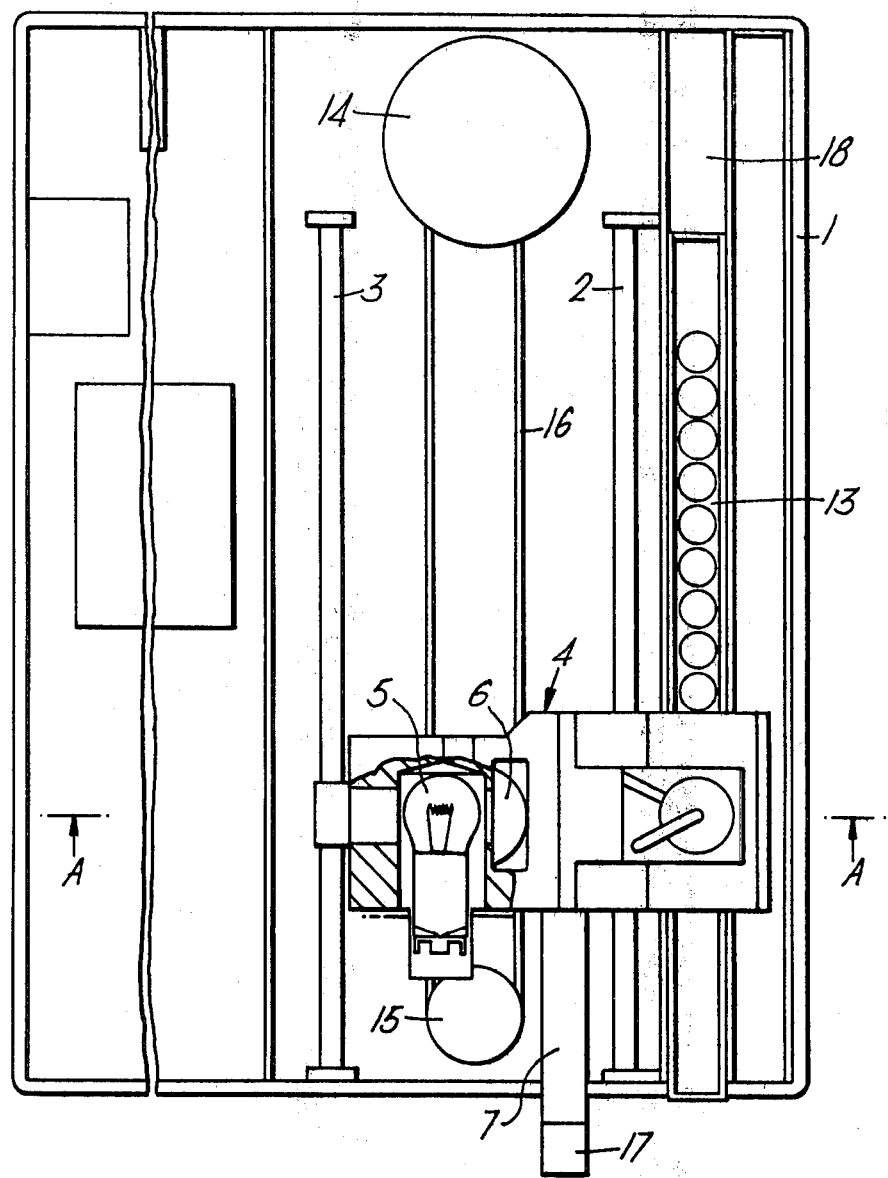

| United States Patent [19] | [11] 4,439,039 |
| --- | --- |
| Suovaniemi | [45] Mar. 27, 1984 |

[54] PHOTOMETER

[75] Inventor: Osmo A. Suovaniemi, Helsinki, Finland

[73] Assignee: Eflab Oy, Helsinki, Finland

[21] Appl. No.: 359,674

[22] PCT Filed: Jul. 10, 1981

[86] PCT No.: PCT/FI81/00055

§ 371 Date: Mar. 9, 1982

§ 102(e) Date: Mar. 9, 1982

[87] PCT Pub. No.: WO82/00361

PCT Pub. Date: Feb. 4, 1982

[30] Foreign Application Priority Data

Jul. 11, 1980 [FI] Finland .................................. 802221

[51] Int. Cl.³ ............................................ G01N 21/27
[52] U.S. Cl. ...................................... 356/416; 356/435
[58] Field of Search ........................ 356/39, 409–411, 356/414, 416, 432, 433, 434, 435, 436, 437, 440, 444; 250/573–576

[56] References Cited

U.S. PATENT DOCUMENTS 3,538,337 11/1970 Hrdina ............................ 356/435 X
4,201,478 5/1980 Gerlier et al. ................... 356/409 X

FOREIGN PATENT DOCUMENTS 2218134 10/1972 Fed. Rep. of Germany .
2618233 11/1977 Fed. Rep. of Germany .
36747 2/1968 Finland .
WO80/00188 2/1980 PCT Int'l Appl. .
367254 5/1974 Sweden .
7705864 11/1977 Sweden .
369299 6/1963 Switzerland ..................... 356/432
516156 1/1972 Switzerland .
1183472 3/1970 United Kingdom ............... 356/432

Primary Examiner—F. L. Evans
Attorney, Agent, or Firm—Hopgood, Calimafde, Kalil, Blaustein & Judlowe

[57] ABSTRACT

The subject of the present invention is a photometer, which comprises a source of light (5), from which the measurement light is arranged to be passed through a lens (6) and a filter (7) onto a semi-transparent mirror (8) placed on the path of the light preferably at an angle of 45°, the reference beam of light (9) being arranged as passing through the said mirror onto a reference detector (11) and the measurement beam of light (10) reflected from the said mirror being arranged as passing to the measurement detector (12). According to the invention, the said source of light (5), lens (6), filter (7), semi-transparent mirror (8), and the reference detector (11) and the measurement detector (12) are placed in an optics frame (4) of one piece, the said optics frame being movable in relation to the frame and case part (1) of the photometer along one or several guides (2, 3). The track of movement of the optics frame consists of linear movement back and forth, the length of the movement corresponding the length of the in-line cuvette set (13) to be measured by means of the photometer.

3 Claims, 2 Drawing Figures

PHOTOMETER

The subject of the present invention is a photometer, which comprises a source of light, from which the measurement light is arranged to be passed through a lens and a filter onto a semi-transparent mirror placed on the path of the light preferably at an angle of 45°, the reference beam of light being arranged as passing through the said mirror onto a reference detector and the measurement beam of light reflected from the said mirror being arranged as passing to the measurement detector.

The object of the invention is to provide a photometer that is handy in use, has small external diameters and compact construction. The photometer in accordance with the invention is mainly characterized in that the said source of light, lens, filter, semitransparent mirror, and the reference detector and the measurement detector are placed in an optics frame of one piece, the said optics frame being movable in relation to the frame and case part of the photometer along one or several guides.

Figure 2:
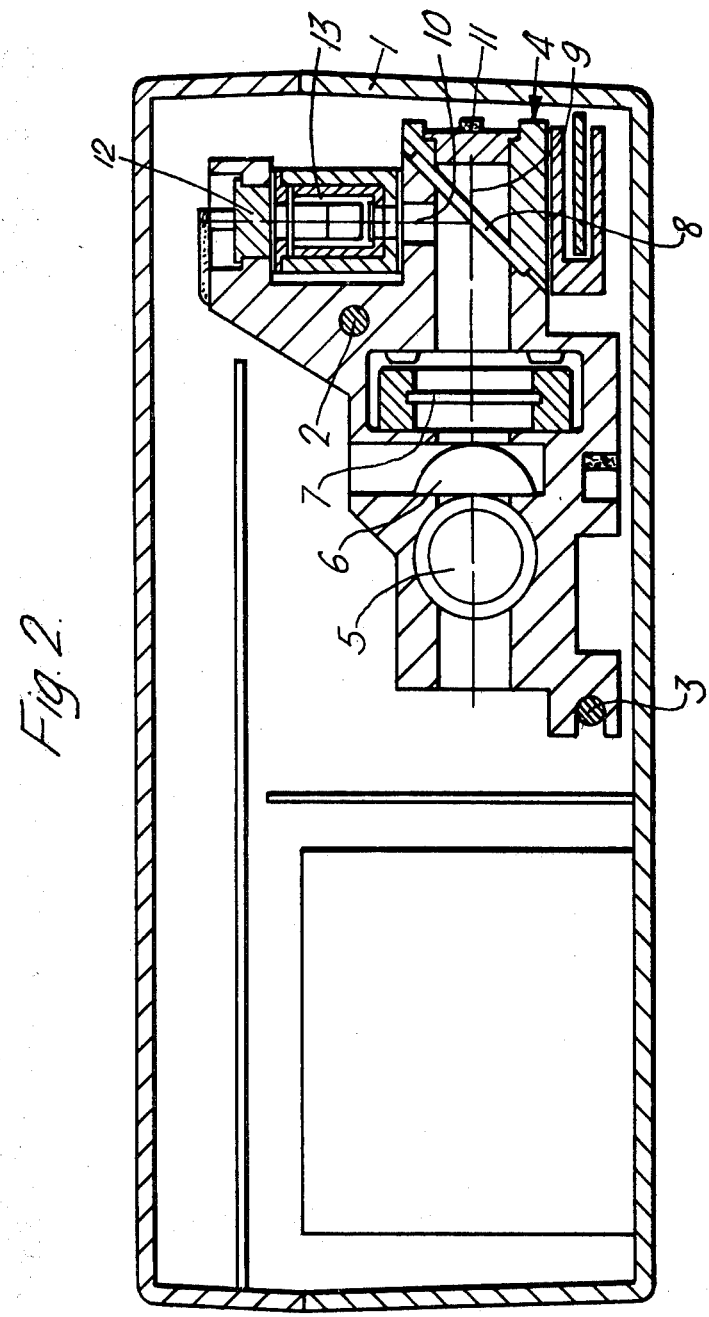

The invention comes out more closely from the following description and from the attached drawings, wherein FIG. 1 shows the photometer as a top view with the cover structure of the photometer removed and FIG. 2 shows a section along line A—A in FIG. 1.

As is shown in FIGS. 1 and 2, horizontal guides 2 and 3 are fitted in the frame and case part 1 of the photometer, the optics frame 4 being arranged as movable along the said guides. The shifting of the optics frame 4 along the guides 2 and 3 can take place, e.g., by means of a cogbelt 16 fitted between an electric motor 14 suitable for the purpose and a pulley 15, the cogbelt 16 being at one point fastened to the optics frame 4. The operation of the electric motor 14 is controlled by means of some automatic control system suitable for the purpose.

A source of light 5, a lens 6, a filter 7, a semi-transparent mirror 8, a reference detector 11, and a measurement detector 12 are fitted onto the optics frame movable in relation to the frame and case part 1. The beam of light from the source of light 5 through the lens 6, the filter 7 and the semi-transparent mirror 8 is passed horizontally to the reference detector 11. The vertical measurement beam of light 10 reflected from the semi-transparent mirror 8 is, in the example case shown by the figures, passed through the bottom of the cuvette to be measured, out of the cuvette set 13, and through the liquid to be measured in the cuvette to the measurement detector 12. The results from the reference detector 11 and from the measurement detector 12 are produced as an output and processed in a known way. The handle portion 17 of the filter unit 7 projects to the side of the frame and case part 1 to the outside so that the filter can be easily replaced in the optics frame 4 by just pulling the filter 7 out and by pushing another filter into its place. The semi-transparent mirror 8 is placed preferably at an angle of 45° in relation to the horizontal plane and to the beam of light coming from the lamp 5 so that the measurement beam of light 10 is reflected from the mirror 8 straight upwards.

Between the semi-transparent mirror 8 and the measurement detector 12 there is an open space in the optics frame for the in-line cuvette set 13 to be measured, pushed into the sample channel 18 in the frame and case part 1. The cuvette set 13 is pushed from the side of the photometer into the sample channel 18 into a specified position, where the cuvette set 13 remains stationary throughout the entire process of measurement, whereas the optics frame 4 is shifted manually or mechanically in relation to the stationary object of measurement, i.e. alternatingly onto each cuvette to be measured out of the cuvette set 13.

If the cuvette set were shifted in relation to a stationary optics part, which is normally the case, the track along which the cuvette set is shifted must be at least twice as long as the cuvette set. When the cuvette set is stationary and the optics part is shifted in relation to the cuvette set, the required maximum length of movement is equal to the length of the cuvette set. Since the maximum dimension of the photometer is determined in accordance with the length of the cuvette set, the photometer can be made a device of a very small size and highly compact.

What is claimed is:

1. A photometer comprising:
   a case having guide means disposed therein;
   means disposed in said case for holding a plurality of linearly arranged stationary samples to be measured;
   a one-piece optics frame displaceably mounted along said guide means to be displaced proximate to each of the samples to be measured, said optics frame including a horizontally disposed light source, light filtering means and a semi-transparent mirror disposed at a 45° angle to provide a vertical measurement beam and a horizontal reference beam, an opening in said optics frame dimensioned so that said means for holding said samples and said samples may pass therethrough, a reference detector for measuring the light of said reference beam disposed horizontally from said light source and a measurement detector disposed vertically above said semi-transparent mirror and said opening in said optics frame.

2. The photometer as claimed in claim 1, further including means for displacing said optics frame.

3. The photometer as claimed in claim 2, wherein said displacing means comprises belt drive means coupled to said optics frame.

* * * * *